US008235932B2

(12) United States Patent
Becker

(10) Patent No.: US 8,235,932 B2
(45) Date of Patent: Aug. 7, 2012

(54) SIDE-BY-SIDE LACRIMAL INTUBATION THREADER AND METHOD

(76) Inventor: Bruce B. Becker, Malibu, CA (US)

( * ) Notice: Subject to any disclaimer, the term of this patent is extended or adjusted under 35 U.S.C. 154(b) by 793 days.

(21) Appl. No.: 12/351,746

(22) Filed: Jan. 9, 2009

(65) Prior Publication Data
US 2010/0179468 A1 Jul. 15, 2010

(51) Int. Cl.
A61M 5/00 (2006.01)
A61B 19/00 (2006.01)
A61F 2/04 (2006.01)
(52) U.S. Cl. ............... 604/8; 128/898; 623/23.7
(58) Field of Classification Search .......... 604/8, 9, 604/11, 12, 27–29, 93.01, 94.01, 164.01, 604/264; 128/887, 898; 623/23.7
See application file for complete search history.

(56) References Cited

U.S. PATENT DOCUMENTS

| 1,906,678 | A | 5/1933 | Wappler |
| 4,305,395 | A | 12/1981 | Martinez |
| 4,380,239 | A | 4/1983 | Crawford et al. |
| 4,756,708 | A | 7/1988 | Martin |
| 5,169,386 | A | 12/1992 | Becker et al. |
| 5,318,513 | A | 6/1994 | Leib et al. |
| 5,997,562 | A | 12/1999 | Zadno-Azizi et al. |
| 6,083,188 | A | 7/2000 | Becker |
| 6,113,567 | A | 9/2000 | Becker |
| 6,238,364 | B1 | 5/2001 | Becker |
| 6,383,192 | B1 | 5/2002 | Kurihashi |
| 6,605,108 | B2 | 8/2003 | Mendius et al. |
| 7,559,925 | B2 | 7/2009 | Goldfarb et al. |
| 7,846,124 | B2 * | 12/2010 | Becker ............... 604/8 |
| 2006/0020248 | A1 | 1/2006 | Prescott |
| 2006/0173482 | A1 | 8/2006 | Melker |
| 2007/0299462 | A1 | 12/2007 | Becker |
| 2008/0306428 | A1 | 12/2008 | Becker |

FOREIGN PATENT DOCUMENTS

| JP | 2005013698 | 1/2005 |
| JP | 2005319190 | 11/2005 |
| WO | 2007139919 | 12/2007 |
| WO | 2008127994 A1 | 10/2008 |

* cited by examiner

Primary Examiner — Tatyana Zalukaeva
Assistant Examiner — Philip R Wiest
(74) Attorney, Agent, or Firm — Charmasson, Buchaca & Leach, LLP

(57) ABSTRACT

A device to facilitate insertion or threading of a flexible silicone intubation stent into the lacrimal drainage system of a patient. The device has an oblong hollow semi-rigid probe having the flexible stent releasably secured to its blunted distal end. The probe and stent are oriented in a side-by-side configuration and inserted endwise through the punctal opening, down through the nasolacrimal duct and into the nasal cavity. The flexible stent is detached from the distal end of the probe, and the probe withdrawn, leaving the stent in place. The flexible stent can be temporarily secured to the distal end of the probe through a number of means. One preferred way is to friction fit a resilient distal aperture of the stent upon the distal end of the probe and occlude the probe's distal opening. The stent is detached by injecting a pressurized fluid through the channel of the probe thereby forcing the distal end of the stent to pop off. The proximal extremity of the stent is secured in the patient by an integrated or separate punctal anchor.

18 Claims, 8 Drawing Sheets

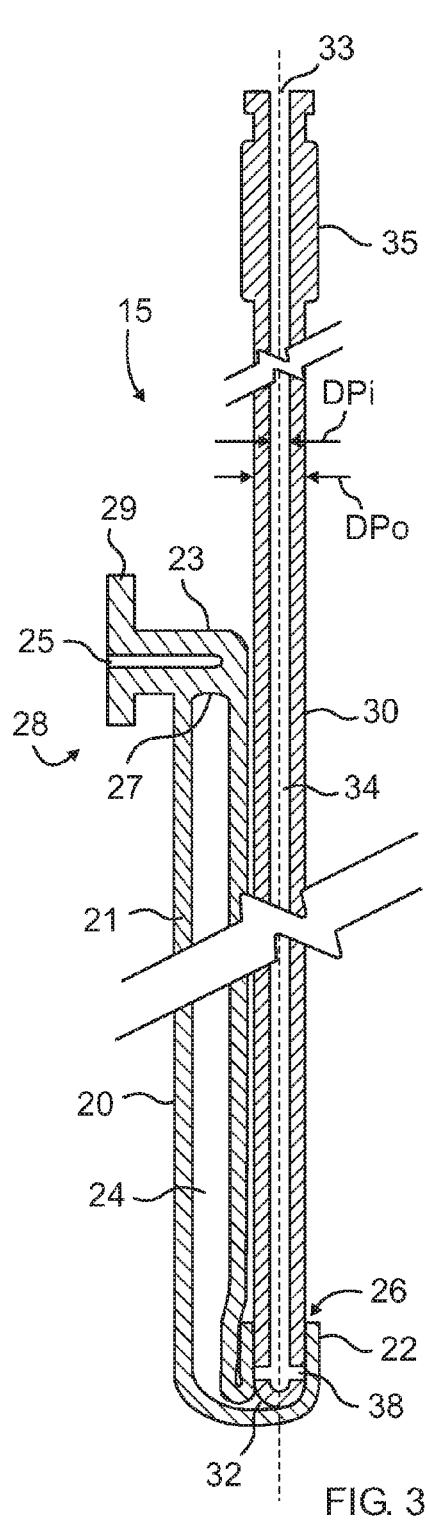
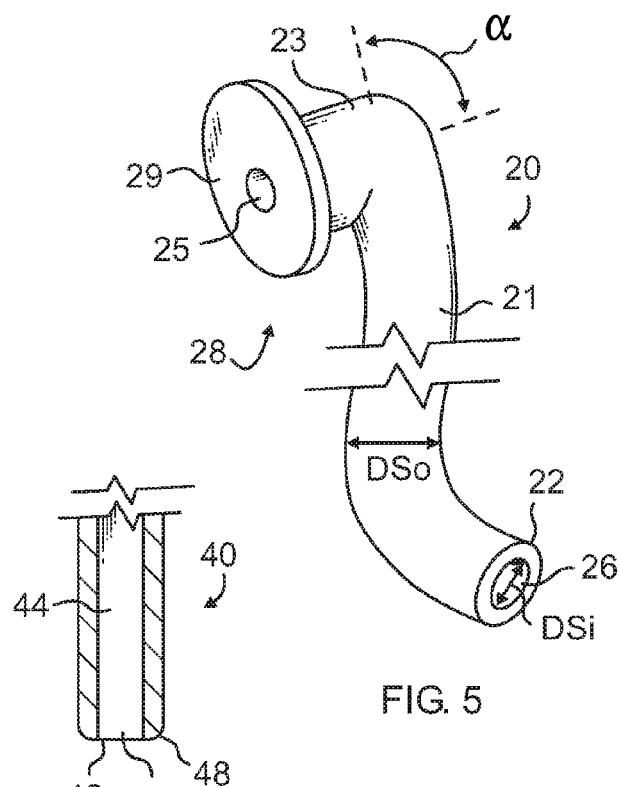
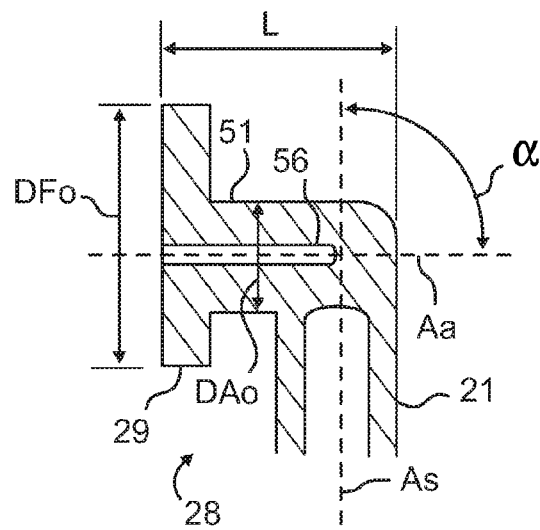

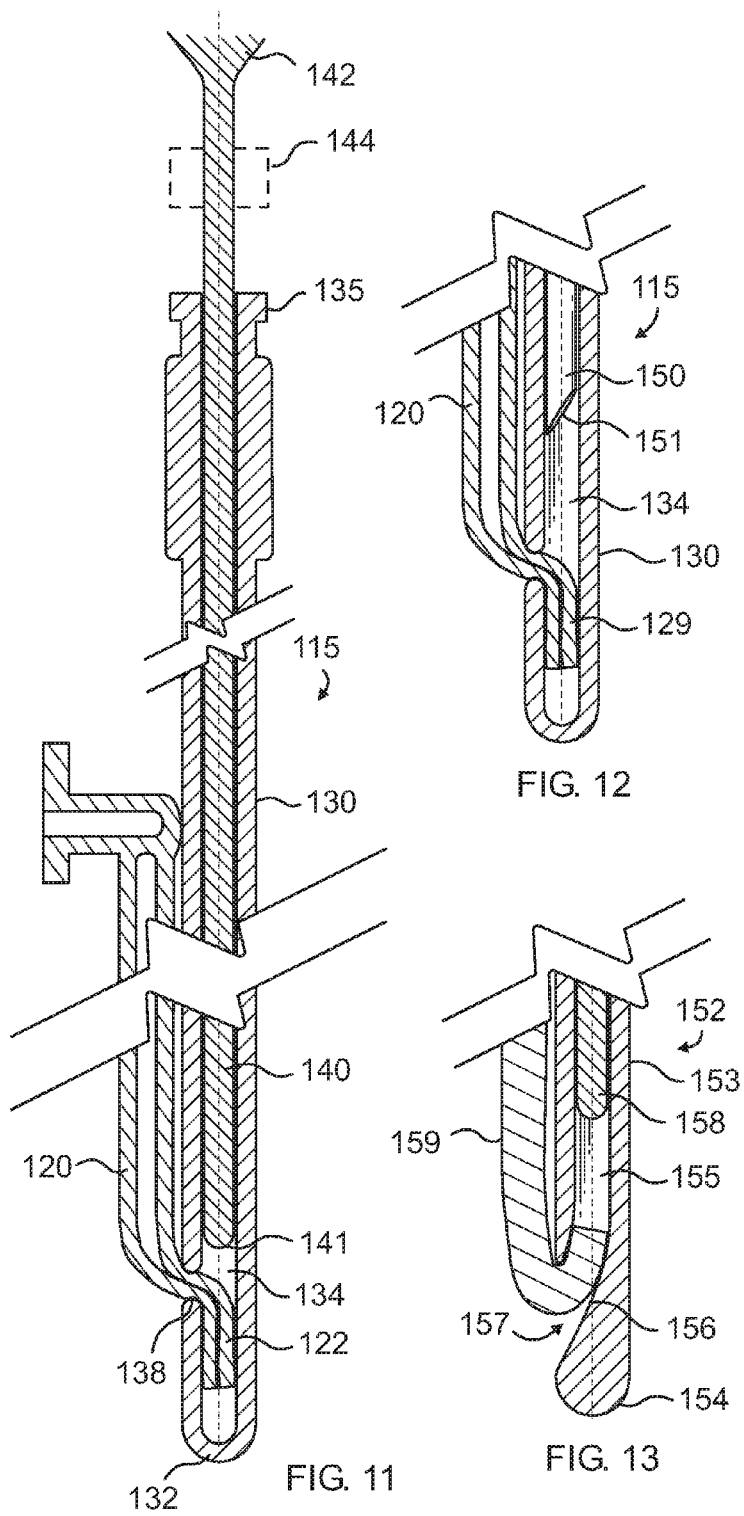

SIDE-BY-SIDE LACRIMAL INTUBATION THREADER AND METHOD

FIELD OF THE INVENTION

The present invention relates to devices used for normalizing the flow of fluid in tubular organs of human bodies that have been damaged by a disease or an accident. More specifically, the invention relates to treating punctal, canalicular and nasolacrimal duct damage, stenosis or obstruction.

BACKGROUND

The orbital portion of the lacrimal gland is located in the superotemporal orbit and the palpebral portion of the lacrimal gland is located on the posterior surface of the superotemporal upper lid. The lacrimal gland produces the aqueous portion of the tear film. Ductules from the orbital portion of the lacrimal gland pass through the adjacent palpebral lacrimal gland to empty in the superior conjunctival cul-de-sac. Smaller accessory lacrimal glands in the upper and lower lids also contribute to tear production. The tears bathe the surface of the eye and then drain into the nose via the lacrimal drainage system.

Referring now to FIGS. 1 and 2, the lacrimal drainage system comprises a pair of small openings, namely the superior punctum 2 and inferior punctum 3, are located on the medial upper and lower lids of the eye 1. Tears flow into these puncta which lead to two small diameter delicate tubes, namely, the superior canaliculus 4 and the inferior canaliculus 5. The canaliculi join together as a short common canaliculus 6 that enters into the larger lacrimal sac 7. The tears then flow from the lacrimal sac down the nasolacrimal duct 8 and out an opening 9 which empties into the nose on the lateral nasal wall 10 and on to the nasal floor 11 beneath the inferior turbinate 12. This space beneath the inferior turbinate is called the inferior meatus 13 of the nasal cavity.

The canaliculi can become obstructed or stenotic on a congenital basis, or acquired as a result of some trauma such as lacerations, inflammation, side effects of chemotherapy, such as taxotere or five-fluorouracil—which may also affect the nasolacrimal duct—or the obstruction can be idiopathic. Once obstructed, tears can no longer drain from the surface of the eye through the lacrimal drainage system into the nose. As a result tears well up in the eye, and run down the face. Excess tears blur the vision and the patient has to constantly dab the eye.

The nasolacrimal duct can be obstructed on a congenital basis, occurring in about 2% to 6% of newborns, or acquired as a result of some trauma, sarcoidosis or other diseases, but most commonly is idiopathic. When the nasolacrimal duct is obstructed, tears stagnate in the lacrimal sac where bacteria multiply leading to infection. The result is a painful enlargement of the lacrimal sac swollen with pus, and a discharge over the eye.

A congenital nasolacrimal duct obstruction often resolves spontaneously, or with the use of antibiotic drops and massage of the lacrimal sac. However, a significant number of patients require surgical treatment.

Canalicular obstruction or stenosis, and nasolacrimal duct obstructions are often treated by forming a passageway through the obstruction or stenotic tissue using a surgical probe which is a small diameter, blunt-ended rod made of solid steel, bronze, silver or other metal. A flattened area in the center of the probe facilitates its manipulation.

The passageway through the nasolacrimal duct can be further dilated using a balloon catheter through dacryocystoplasty (DCP). Often the treatment of nasolacrimal duct obstruction in adults involves the creation of a new passage from the lacrimal sac directly into the nasal cavity bypassing the nasolacrimal duct according to a procedure called dacrocystorhinostomy (DCR). Both procedures are disclosed in my U.S. Pat. No. 5,169,386 incorporated herein by this reference.

Intubation or stenting of the lacrimal system is often performed after lacrimal surgery or as a primary treatment for nasolacrimal duct obstruction, canalicular stenosis, or canalicular laceration, in order to keep the lacrimal drainage passageway open and prevent scars from permanently clogging the canaliculi or nasolacrimal duct.

In this specification the term "intubation" is meant to include the insertion of both tubular and non-tubular oblong flexible devices into the lacrimal drainage system in order to keep the passageway open regardless of whether tears flow through a tubular device or around a non-tubular device. Since tears typically flow around the device whether it is tubular or not, the term "stent" in this specification is used to collectively refer to a tubular or non-tubular device remaining inserted in the lacrimal drainage system after an intubation process has been performed.

In cases of canalicular or nasolacrimal duct obstruction from chemotherapy, intubation is performed as quickly as possible to prevent complete, irreversible closure. Intubation typically involves placement of a flexible silicone tube looped through both canaliculi where both ends extend down the nasolacrimal duct and into the nose. Such intubation is described in Martinez, U.S. Pat. No. 4,305,395, and Crawford et al., U.S. Pat. No. 4,380,239, both of which are incorporated herein by this reference.

A number of types of intubation devices are available. The most common type is a silicone tube having a metal probe attached on each end as in Crawford et al. cited above. A probe on one end is pushed through one of the punctum, its canaliculus, the lacrimal sac, and down the nasolacrimal duct into the nose. The probe is grasped in the nose by the surgeon and pulled out the naris. The tube follows the probe. The probe on the other end of the tube is pushed through the second punctum, its canaliculus, the lacrimal sac, and down the nasolacrimal duct into the nose, grasped by the surgeon, and pulled out the naris bringing the other end of the tube with it. The probes are removed and the two ends of the tube are tied together and left hanging in the nose. The tube is removed several months later by pulling it up the lacrimal system, cutting it, and removing it through one of the puncta.

The above process presents several difficulties. First, the nasal opening to the nasolacrimal duct is extremely difficult to visualize during surgery or examination, and very difficult to access with an instrument, making the grasping of the probe difficult. Rigid and flexible endoscopes usually cannot fit between the inferior turbinate and the lateral nasal wall. Direct visualization using a nasal speculum and a headlight is usually not possible. Placing an instrument near the nasolacrimal duct opening through the nose can be very difficult. A probe or tube sticking out of the nasolacrimal duct opening in the nose will often be buried in the surrounding soft tissue of the nasal floor or lateral wall. Further, there is often edema of the inferior turbinate and nasal mucosa, and sometimes bleeding which make it more difficult to locate, access, grasp, and retrieve the probe, tube, suture or other item coming out of the nasolacrimal duct opening. It is often difficult if not impossible to position a suction catheter in the inferior meatus in order to remove blood around the nasolacrimal duct opening.

One way of trying to confirm without visualization whether the probe, tube or other item has penetrated into the nose is by touch. The surgeon will typically introduce a metal instrument through the external naris into the nose and try blindly to touch the tip of the item sticking out of the nasolacrimal duct opening until a contact between the two is felt. Detecting contact takes quite a bit of skill and experience. Often, if no contact is felt, the surgeon may remove the item and reinsert it, then try again to confirm penetration. These repeated procedures can cause multiple traumas to the lacrimal drainage system.

Another commonly used intubation device is the MINI-MONOKA device available from FCI Ophthalmics Inc. of Marshfield Hills, Mass. (hereinafter "FCI"). This device consists of a short silicone tube which is generally not long enough to extend into the nasolacrimal duct. The proximal end of the tube is formed into a punctal plug to anchor it in a punctum. The tube is threaded through a punctum and canaliculus into the lacrimal sac, and can be used to stent the canaliculus but typically not the nasolacrimal duct.

Another type of intubation device is the MONO-CRAWFORD device available from FCI which is similar to the MINI-MONOKA device but provides a longer flexible stent. It also has a punctal plug at its proximal end. The distal end must be threaded through the lacrimal system from the eye side but is too flexible to be pushed on its own through the system.

The RITLENG probe, also available from FCI, has been designed to help this problem. It is a hollow metal guide tube with a slit-like opening along its entire length which is placed through the punctum, canaliculus, lacrimal sac, and down the nasolacrimal duct into the nose. A separate polyethylene tube that is attached to a flexible silicone tube having a punctal plug formed on its proximal end is threaded through the guide into the nose. The polyethylene tube is located and grasped in the nose by the surgeon and pulled out the naris. The guide is then withdrawn out the punctum. The silicone tube passes through the slit so that the guide can be removed. The plug on the proximal end of the silicone tube is then seated in the punctum. The distal end of the silicone tube is then cut just inside the external naris. Therefore, the RITLENG tube must be retrieved and pulled out the nose. This can be difficult or impossible in some cases as detailed above.

Both the MINI-MONOKA and RITLENG devices use punctum plugs integrally formed onto the proximal ends of flexible tubes. Therefore, the length of the tube can only be altered during surgery by cutting the distal end. The RITLENG and MONO-CRAWFORD tubes must be retrieved in the nose and brought out the nose to achieve this. The MINI-MONOKA tube is too short to have its length altered in vivo.

My U.S. patent application Publication No. 2007/0276314 incorporated herein by this reference describes a silicone tube with a balloon on the end. It extends from the punctum and canaliculus into the lacrimal sac. A balloon on the end of the tube in the lacrimal sac is then inflated to keep the tube in position. The tube does not extend into the nasolacrimal duct.

The FCI company has a plug that is placed in the punctum in order to obstruct the punctum and prevent tear drainage through the lacrimal system into the nose. This is used for patients with dry eye syndrome to keep more tears in the tear film over the eye. The FCI plug has a lumen with a proximal opening and a distal closed end. A metal probe at the end of an inserter stretches the tube along its longitudinal axis to reduce the diameter during insertion. When the plug is in place, the inserter is withdrawn and the plug contracts along its longitudinal axis and thus increases radially so that it will be snug in the punctum and not fall out. The lumen does not expand. The device is not expanded radially by the inserter, but rather is expanded longitudinally which decreases its outside and inside diameter.

I show in International Publication No. WO 2007/139919 a lacrimal stent that uses a soft tube, ideally silicone, that has a higher durometer reinforcer tube within the closed distal end. The silicone stent can be placed in the lacrimal system through the punctum, canaliculus, common canaliculus, lacrimal sac, and nasolacrimal duct into the nose. The silicone tube and reinforcer have holes in the sidewalls in the distal end. A hollow irrigating probe having holes in the sidewalls is used to push the silicone tube into the lacrimal system and the distal end into the nose. The irrigating probe allows fluorescein stained fluid to be irrigated through the tube and recovered in the nose to confirm that the silicone tube has penetrated all obstructions and reached the nasal cavity. The reinforcer resists the probe puncturing the distal end of the silicone tube. The silicone tube does not need to be retrieved in the nose.

There are however, certain problems that have been encountered. If there is a very tight nasolacrimal duct or canaliculus, then the probe may still puncture through the end of the silicone tube and reinforcer or otherwise rupture the tube. In this event it is impossible to emplace the silicone tube in the lacrimal system.

Another problem is that the distance from the punctum through the lacrimal system to the nasal floor is quite variable between and within age groups, and it is often difficult to predict the proper length of the stent to be used. Furthermore, the angle at which the silicone tube and enclosed probe exit the nasolacrimal duct in the nose is different among patients. The angle of exit determines where the probe and tube hit the nasal floor. This is because the nasal floor is concave upward where it comes off the lateral nasal wall. The point at which the probe and tube hit the nasal floor is a factor in determining the length of silicone tube needed. Silicone tubes of many different lengths must be available for the surgeons's use for these reasons.

The instant invention results from attempts to avoid the aforesaid problems and provide more efficient, simpler and safer devices and procedures in the treatment of nasolacrimal duct obstructions.

SUMMARY

The instant embodiments provide devices and method to better treat obstructions in the nasolacrimal system.

In some embodiments there is provided a method for placing a stent in a patient's nasolacrimal duct which comprises the steps of: selecting an elongated semirigid tubular probe and an elongated flexible stent; wherein said probe has a proximal end and a distal end; wherein said stent has a proximal extremity and a distal extremity; wherein said distal extremity is detachably secured to said distal end; and, wherein said probe and said stent are oriented in a side-by-side configuration; pushing said distal end and said distal extremity through a patient's punctum, canaliculus, lacrimal sac, nasolacrimal duct and into the nasal cavity; detaching said distal extremity from said distal end while said distal end is located in said cavity; proximally withdrawing said probe while leaving said distal extremity in said cavity; and, placing a punctal anchor associated with said proximal extremity within said patient's punctum.

In some embodiments the method further comprises: said probe having an internal channel, and a first opening to said channel near said proximal end; and a second opening to said channel near said distal end; and, wherein said stent occludes said second opening of said channel.

In some embodiments the second opening comprises an axial hole extending through an endwall of said probe to said channel.

In some embodiments the second opening comprises at least one radial hole extending through a sidewall of said probe to said channel.

In some embodiments the step of selecting an elongated flexible stent further comprises: choosing said stent to be tubular; and, said distal extremity is open, and shaped and dimensioned to snugly fit over said distal end of said probe.

In some embodiments the step of detaching comprises: injecting a fluid into said channel at a pressure sufficient to overcome a force detachably securing said distal extremity to said distal end.

In some embodiments the step of detaching comprises: inserting a rod into said channel and contacting said distal extremity at a pressure sufficient to overcome a force detachably securing said distal extremity to said distal end.

In some embodiments the step of selecting comprises: determining a given length for said stent, wherein said determining comprises measuring a distance from said punctum to said nasal cavity; wherein said measuring comprises: inserting a graduated probe through said punctum to said nasal cavity; confirming a distal end of said graduated probe is located in said nasal cavity, and, identifying a graduation mark on said graduated probe closest to the punctal opening.

In some embodiments the method further comprises: stiffening said probe prior to said pushing; wherein said stiffening comprises: engaging said channel with an oblong rod having a first flexural rigidity which is more rigid than a second flexural rigidity of said stent.

In some embodiments the step of selecting of said probe comprises: choosing said probe to have at least one radial hole near said distal end of said probe and wherein said distal extremity engages said hole.

In some embodiments the step of detaching comprises pushing a stylet into said channel to cut said stent.

In some embodiments the method is practiced in absence of retrieving a portion of said stent out the naris.

In some embodiments the method is practiced in absence of visualizing said stent within said nasal cavity.

In some embodiments the method is practiced in absence of shortening said stent in vivo.

In some embodiments the step of placing a punctal anchor occurs during said pushing step.

In some embodiments the method further comprises: confirming that the distal end is located in said nasal cavity; wherein said confirming comprises: injecting a tracing fluid through the probe; and recovering traces of said fluid in said nasal cavity.

In some embodiments the method further comprises injecting medication into said system through said probe.

In some embodiments there is provided a method for stenting a passageway formed by dacryocystorhinostomy ("DCR") which comprises the steps of: selecting an elongated tubular probe and an elongated flexible stent; wherein said probe has an open proximal end and an open distal end, and defines an internal channel; and, wherein said stent has a proximal extremity and a distal extremity; and, wherein said distal extremity is detachably secured to said distal end; pushing said probe carrying said stent through said passageway and into the nasal cavity; confirming that the distal end of said probe is located in said nasal cavity; detaching said distal extemity from said distal end; proximally withdrawing said probe while leaving said stent in place; and, placing a punctal anchor associated with a proximal extremity of said stent within said patient's punctum.

In some embodiments there is provided a multi-functional surgical tool for the treatment of nasolacrimal obstruction, stenosis or damage which comprises: a first elongated semi-rigid tubular probe having proximal and distal ends; an elongated stent having proximal and distal extremities; wherein said distal extremity is releasably secured to said distal end; wherein said probe and said stent are oriented in a side-by-side configuration; a punctal anchor associated with said proximal extremity of said stent; and, wherein said anchor is sized and shaped to intimately and oversizedly engage said punctum.

In some embodiments the probe is shaped and dimensioned to define an internal channel; said probe has a first opening to said channel near said proximal end; and a second opening to said channel near said distal end; and, said stent occludes said second opening of said channel.

In some embodiments the second opening comprises an axial hole.

In some embodiments the second opening comprises a radial hole.

In some embodiments the second opening comprises a pair of radial holes extending through a sidewall of said probe to said channel.

In some embodiments the stent has a distal aperture shaped and dimensioned to snugly and releasably engaged by said distal end to form a friction fit.

In some embodiments the probe has a distal opening shaped and dimensioned to snugly and releasably engaged by said distal extremity to form a friction fit.

In some embodiments the tool further comprises a first connector at a proximal end of said probe adapted to releasably connect to a pressurized fluid source.

In some embodiments the source emits an amount of fluid at a pressure sufficient to overcome a static friction bond between said stent and said probe.

In some embodiments the tool further comprises a first rod diametrically sized to engage said channel of said probe.

In some embodiments the rod dimensioned to contact a portion of said stent occluding said second opening.

In some embodiments the rod has distal cutting surface oriented to cut said stent through axial movement of said rod with respect to said probe.

In some embodiments of the tool: said probe has a first length; said stent has a second length shorter than said first length; and, wherein said second length is between about 10 millimeters and about 100 millimeters.

In some embodiments the probe has a maximum cross-sectional dimension of between about 0.014 inch and about 0.060 inch.

In some embodiments the probe further comprises graduation marking on an outer surface portion located at a range of distances from said distal end corresponding to a common range of anatomical distances between a punctum and a nasal floor.

In some embodiments the probe has a first flexural rigidity allowing it to be introduced into a patient's nasolacrimal duct through one of said patient's canaliculi by pushing on portions of said probe located proximal to said one of said patient's canaliculi; and, said stent having a second flexural rigidity less rigid than said first rigidity.

In some embodiments the anchor has radial disuniformity shaped and dimensioned to rest against a medial sidewall of said probe, thereby minimizing a lateral dimension of the probe and stent oriented in said side-by-side configuration.

In some embodiments there is provided a multi-functional surgical tool for the treatment of nasolacrimal obstruction, stenosis or damage which comprises: a first elongated semi-rigid tubular probe having proximal and distal ends, and defining an internal channel; said probe being sized and having a first flexural rigidity to be introduced into a patient's nasolacrimal duct through one of said patient's canaliculi by pushing on portions of said probe located proximal to said one of said patient's canaliculi; an elongated stent having proximal and distal extremities; said stent having a second flexural rigidity; wherein said second rigidity is less rigid than said first rigidity; means for detachably securing said distal extemity to said distal end; and, an anchor sized to intimately and oversizedly engage said punctum.

BRIEF DESCRIPTION OF THE DRAWINGS

FIG. 3 is a cross-sectional side view illustration of a combined probe/stent insertion structure.

FIG. 4 is a partial cross-sectional side view illustration of the distal end of a probe having an axial opening.

FIG. 5 is a diagrammatic perspective illustration of a flexible stent having an integrated punctal anchor and a distal aperture.

FIG. 6 is an enlarged cross-sectional side view illustration of a stent having a temporarily deformable integrated proximal anchor structure.

FIG. 11 illustrates an alternate embodiment of the stent releasably secured through a distal radial opening in the probe.

FIG. 12 illustrates a coaxial stylet engaging the channel of the probe to cut the stent free.

FIG. 13 illustrates a coaxial rod engaging the channel of the probe to push off a channel-engaging stent.

FIG. 14 illustrates a probe having an axial opening and a friction-enhancing outer collar.

FIG. 15 illustrates a probe having an axial opening narrower than its axial channel.

DESCRIPTION OF THE EXEMPLARY EMBODIMENTS

Figure 1:
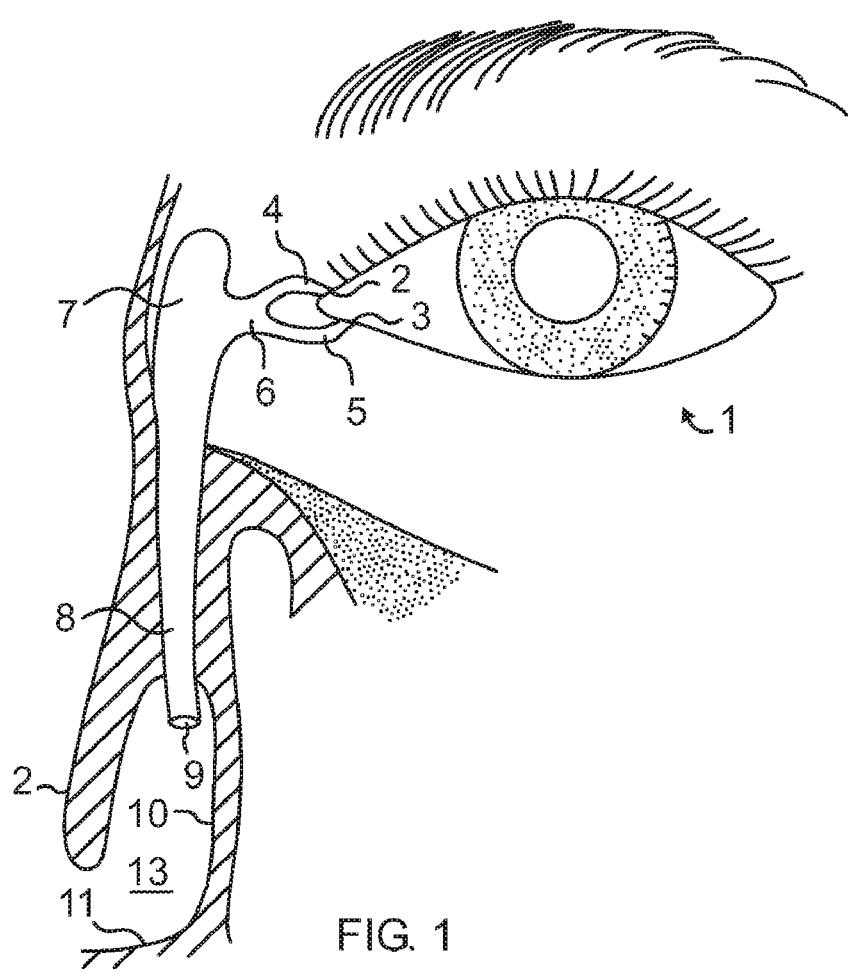
FIG. 1 is a cross-sectional frontal illustration of the lacrimal drainage system of a human patient.
Figure 2:
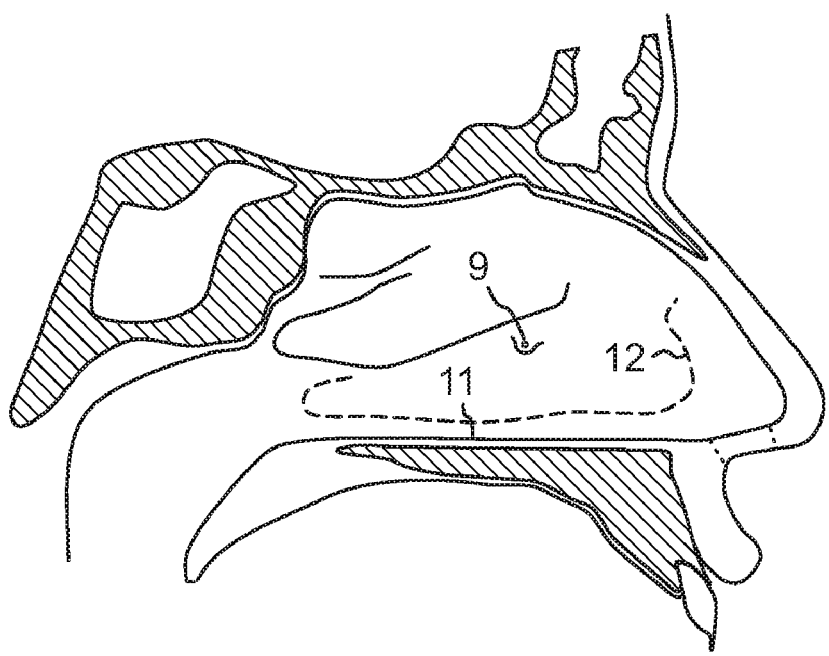
FIG. 2 is a partial, cross-sectional side illustration of the system of FIG. 1.

Referring now to the drawing, there is shown in FIG. 3 a the cross-sectional view of a stent insertion structure 15 for inserting a flexible stent 20 into a patient's lacrimal drainage system from one of the puncta into the nasal cavity. This structure combines an elongated, flexible stent 20 secured in a side-by-side configuration to a semi-rigid, elongated, hollow probe 30. The distal extremity 22 of the stent is releasably secured to the distal end 32 of the probe. The size of the combined structure is selected by the surgeon to allow it to be inserted into the lacrimal drainage system. As the structure is threaded from the punctum to the nasal cavity, the probe pulls the stent along with it. Once emplaced, the stent is detached from the probe and the probe withdrawn. An anchoring structure 27 associated with the proximal extremity 23 of the stent snugly secures the stent to the punctum.

The components of the combined insertion structure 15, primarily the stent 20 and probe 30, are preferably shaped so that they minimize the radial dimensions of the structure and thereby minimize its invasiveness during the insertion procedure. The combined structure is further selected so that the structure has the proper range of rigidity, column strength and resistance to lateral bending that allow it to be used in the procedure described below. In general, it has a slight degree of flexibility resulting from the choice of material and its dimensions to allow it to navigate the bends and angles of the lacrimal system but also has sufficient rigidity to be pushed through the lacrimal system and most encountered stenoses or obstructions into the nasal cavity. This arrangement also allows the probe to bear the insertion forces placed on the combined structure. The preferred flexural rigidity of the entire combined structure will depend on the anatomy of the patient and is selected to provide the above functionality while allowing the surgeon to manipulate the combined structure from the proximal side only. In other words, the surgeon can emplace the combined structure in absence of any guidewire, and while manipulating only those parts of the structure that remain exposed proximally from the punctum. The physical characteristics of the individual components can be selected to accommodate the above defined flexural rigidity requirements.

As shown in FIGS. 3 and 5-6, the stent 20 of this embodiment is formed from a length of flexible tubing made from a biocompatible material such as silicone, polyethylene, or other material known to those skilled in the art. The tubular stent has an oblong body 21 having a distal extremity 22 and a proximal extremity 23. The stent can be substantially hollow, defining a central lumen 24 extending from a distal aperture 26 to a barrier 27 located near the proximal extremity. Alternately, the stent can be solid, in which case the distal aperture terminates in an internal pit. Alternately, the channel can extend, and be in fluid communication with both the distal aperture and a proximal aperture 25.

In this embodiment the distal aperture 26 is shaped and dimensioned to snugly fit over the distal end 32 of the probe 30, thereby securing the stent to the probe by friction fit and occluding a distal opening 38 of the probe leading to its internal channel 34. As will be described below, this friction fit is overcomable so that the surgeon can release the stent from the probe in vivo.

The dimensions of the stent will depend on the anatomy of the patient. For many applications, the preferred stent has an outside diameter DSo of between about 0.50 mm and about 3.00 mm, and can typically be about 0.70 mm, an internal diameter DSi of between about 0.10 mm and about 2.50 mm, and can typically be about 0.37 mm, and a length of between about 10 mm and about 100 mm, and can typically be about 75.0 mm.

The proximal extremity 23 of the stent 20 can be formed into an integrated punctal anchor structure 28. The anchor is shaped and dimensioned to provide a snug fit to the patient's own anatomy near the punctum. In the present embodiment the anchor structure 28 is characterized by a generally cylindrical stem 51 having a proximal end formed into the widened flange or collar 29. The opposite distal end of the stem connects to the stent body 21 at an angle α formed between the axis Aa of the stem and the axis As of the stent body 21. This angle can be between about 0 and about 135 degrees, and is more commonly near 0 or near 90 degrees.

The stem 51 has axial length L of between about 0.2 and about 8.0 mm, and is typically between about 2.0 and about 2.5 mm for most adult human patients. The stem 51 has a resting outside diameter DAo which allows it to fit comfortably in the punctum and adjacent portion of the canaliculus, this diameter will depend on the anatomy of the patient and is preferably between about 0.1 and about 3.0 mm, and is typically between about 0.7 and about 1.0 mm for most adult human patients, the average diameter is ideally about 0.9 mm.

The flange 29 is intended to rest against the lid margin just external to the punctum to keep the anchor from migrating internally. The flange has a generally rounded circular, elliptical or oval shape as seen perpendicular to the stem axis Aa and is dimensioned large enough to keep it from migrating into the punctal lumen, but small enough to avoid irritating the eye. The major dimension DFo of the flange 29 will depend on the anatomy of the patient and is preferably between about 0.020 mm and about 4.0 mm, and is typically between about 1.0 and about 3.0 mm for most adult human patients, the average diameter is often ideally between about 1.75 mm and about 2.5 mm.

The elbow of the transition between the stem 51 and stent body 21 also provides an outward migration resistant structure.

Additionally, the integrated punctal anchor structure 28 can be made to be deformable, further facilitating emplacement. Specifically, the deformable punctal anchor has a very small, closed-ended cylindrical bore 56 extending through the stem 51 from the stent's proximal aperture 25. Although the bore is shown penetrating the anchor in line with the stem axis As, the bore could penetrate from other directions, for example radially. The bore is used by a stretching tool to temporarily and resiliently deform the anchor and facilitate insertion through the punctum. The stretching tool can operate similarly to an inserter used to insert SNUG PLUGS brand punctum plugs available from FCI. The tool has a distal prong which engages the bore of the anchor, and fingers which grasp the collar of the anchor and stretch the anchor axially over the prong. The anchor stem is selected to have a resiliently reducable diameter so that while it is stretched axially, its outside diameter DAo is reduced. The anchor is then inserted using the tool into the punctum and released whereupon it springs back into its "at rest" shape.

Various alternate structures for the anchor are shown in FIGS. 16A-16E described below.

As shown in FIG. 3, the oblong probe 30 is hollow having an internal axial channel 34 extending from a distal end 32 to an open proximal end 33 having a connector 35 such as luer-lock which allows it to be connected to a source of pressurized fluid and provide a convenient grasping point for the surgeon to facilitate manipulation. The distal end 32 of the probe is preferably blunted, having a closed rounded surface which facilitates insertion into the distal aperture 26 of the stent, and discouraging accidental penetration of the probe through the stent wall near its distal extremity. The blunt end also avoids damage to the lacrimal tissues in the event the stent becomes inadvertently dislodged. The bunted end also allows the probe to be used in the initial confirmation and measuring procedure described below in reference to FIG. 7.

The distal end 32 of the probe 30 has at least one opening 38 to allow pressurized fluid in the channel 34 to exit and dislodge the stent 20. The opening can be one or more holes penetrating radially through the side wall of the probe near the distal end as shown in FIG. 3.

The probe 30 is shaped dimensioned and made from materials which allow it to be semirigid so that it imparts the necessary flexural rigidity to the combined stent and probe structure. The probe can be made of stainless steel, Nitinol or other similar material known in the art. Although the probe is made of a rigid or semi-rigid material, its length and the relative thinness of its wall render it somewhat flexible and easily bendable.

The dimensions of the probe 30 will also depend on the anatomy of the patient. For many applications, the preferred probe has an outside diameter DPo of between about 0.014 inch and about 0.060 inch, and typically between about 0.022 inch and about 0.028 inch, an internal diameter DPi of between about 0.010 inch and about 0.046 inch, and typically between about 0.011 inch and about 0.016 inch, and a length of between about 1 and about 15 inches, typically about 4 inches. This results in a wall thickness of between about 0.002 inch and about 0.020 inch, and typically between about 0.006 inch and about 0.008 inch. Those skilled in the art will recognize that subtracting the inner diameter from the outer diameter results in 2 times the wall thickness.

It should be noted that the outer diameter of the probe 30 at the distal end 32 is selected to allow it to intimately and snugly engage the distal aperture 26 of the stent 20 and therefore form a friction fit overcomable by forces applied in vivo when the surgeon desires detachment. Further, the diameter of the central channel of the probe is selected to accommodate the flow of pressurized fluid, and in some embodiments the passage of a rigidizing or disengagement rod and/or a stylet.

Optionally, the probe may have a handle, or a flattened or otherwise enlarged section (not shown) at or near its proximal end, as can be found in many surgical probes, which can be used to facilitate its handling.

As shown in FIG. 4, an alternate embodiment of the probe 40 provides an axial opening 46 to its internal channel 44 at the distal end 42. It will be understood that the distal extremity of the stent can be shaped and dimensioned to snugly fit into the axial opening 46 of the probe rather than over it.

It is noted that use of a radial hole can allow fluid to exit even when the distal axial tip of the probe is closed (as shown in FIG. 3) or is open (as shown in FIG. 4) but blocked by the nasal floor for example.

Referring now to FIGS. 7-10, an exemplary method for emplacing a flexible stent using the above-described structure will be described.

Figure 7:
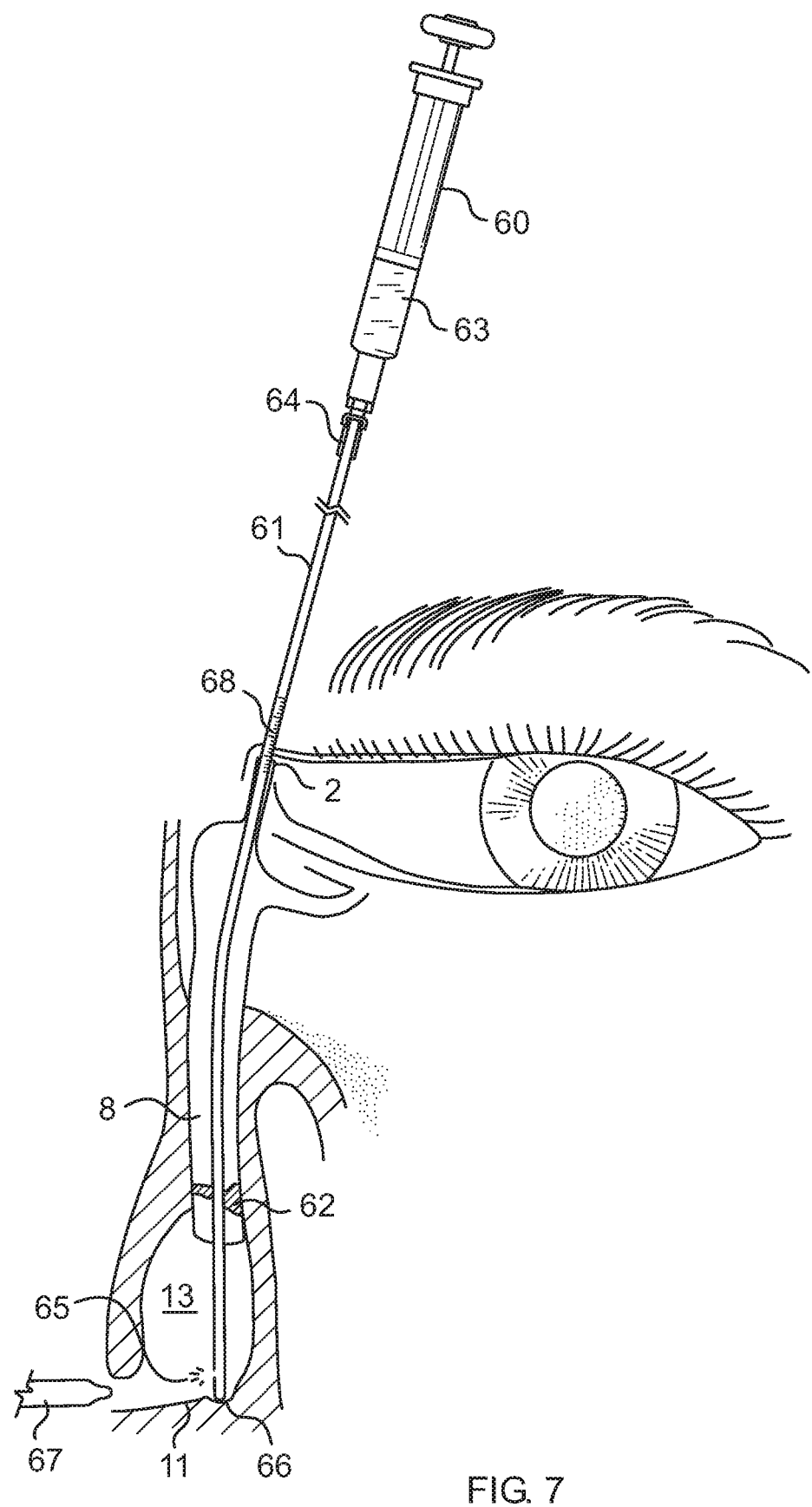
FIG. 7 illustrates the insertion of a hollow graduated irrigating probe into the lacrimal drainage system to confirm a passageway to the nose and to measure the distance from punctum to nasal floor.

As shown in FIG. 7, in order to form or confirm the existence of a passageway through the lacrimal drainage system from a punctum 2 to the nasal cavity 13, an irrigating lacrimal surgical probe 61 is selected and inserted into a punctum 2 and pushed though the nasolacrimal duct 8 and into the nasal cavity 13 of a patient. The surgeon confirms that the irrigating probe has penetrated all obstructions 62 and reached the nasal cavity 13 by connecting a syringe 60 filled with fluorescein-stained fluid 63 to the proximal luer-lock connector 64 on the irrigating probe 61. Fluid is then injected through the probe and out the distal hole 65. The hole punctures radially through the cylindrical wall of the irrigating probe near its distal end 66 so that it remains essentially unblocked even if the distal end touches the nasal floor 11. Optionally, the probe 30 used in the combined stent and probe structure described with reference to FIGS. 3 and 4 can be used, without the stent attached, to confirm the passageway. A probe having two or more distal radial holes can easily discharge fluid when one of the holes is blocked.

The fluid can be suctioned out of the nasal cavity 13 with a soft suction or other suction catheter 67. If the fluorescein-stained fluid irrigates easily and a large volume is suctioned out of the nose, this indicates that the probe has penetrated all obstructions and stenoses and entered the nasal cavity. Otherwise, it is likely that the probe has not adequately penetrated or has followed a false passage. In this case, the probe must either be pushed further down the nasolacrimal duct into the nasal cavity, or the probe must be pulled proximally until its tip is in the lacrimal sac, reoriented and pushed down again through the nasolacrimal duct into the nasal cavity. The same irrigation and suctioning procedures are repeated as describe above until proper penetration has been confirmed.

Once proper penetration has been confirmed the surgeon reads the graduation markings 68 located on the outer surface of the probe 61 and identifies which of the markings is closest to the punctal opening 2. The markings are located at a range of distances from said distal end 66 of the probe corresponding to a common range of anatomical distances between a punctum and the nasal floor 11. From this information the surgeon is able to measure the distance from the punctum to the nasal cavity in this patient and make a selection of the proper given length of stent to be inserted. The irrigating probe is then removed. In this way, the added complication of shortening an over-long stent can be avoided.

The surgeon selects a lacrimal surgical probe and an oblong flexible stent having a given length. The distal extremity of the stent is releasably secured to the distal end of the probe.

Figure 8:
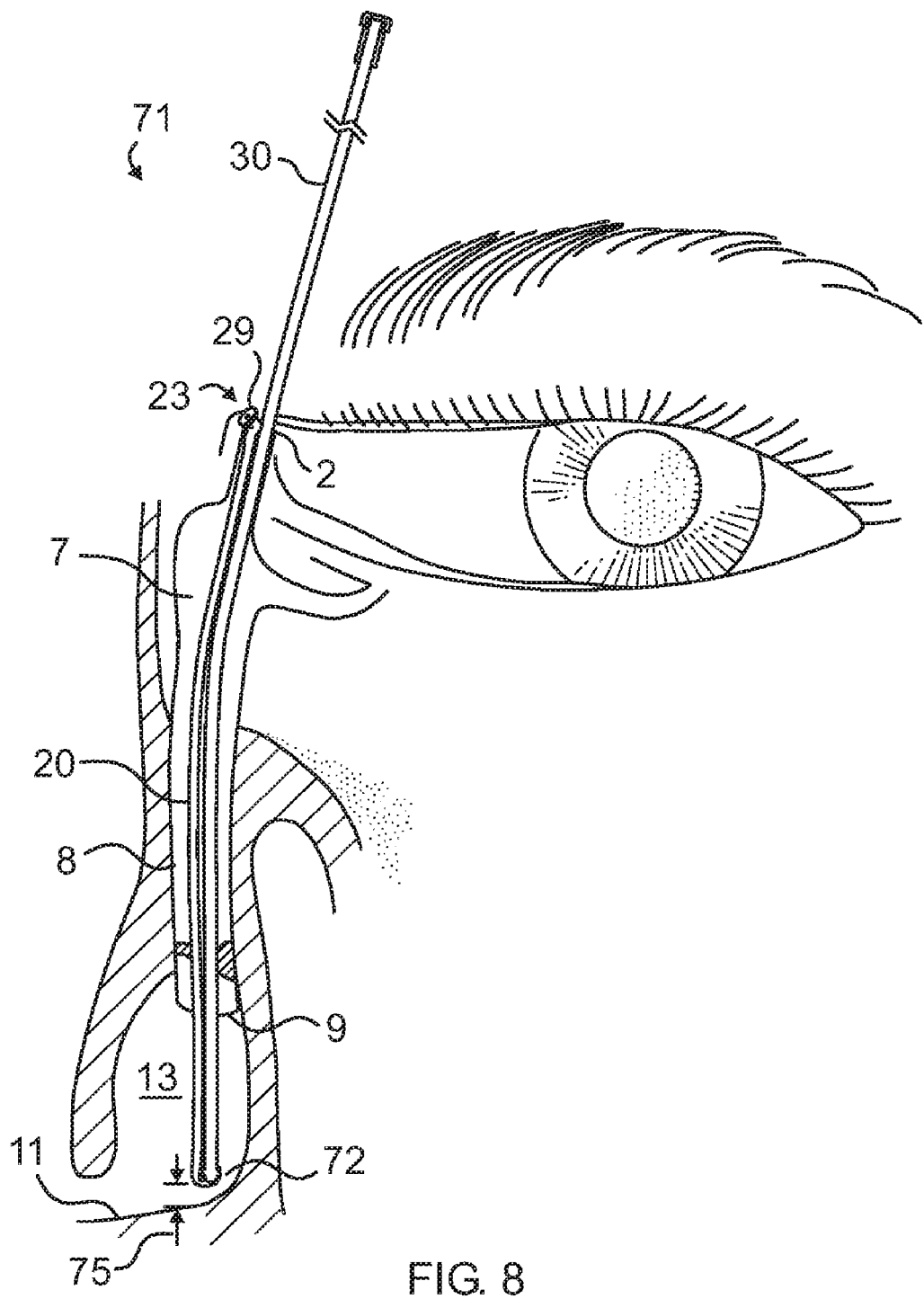
FIG. 8 illustrates the insertion of a side-by-side oriented combined lacrimal probe and stent structure into the lacrimal drainage system.

As shown in FIG. 8, the combined probe and stent structure 71, oriented in a side-by-side configuration, is inserted into the lacrimal drainage system in a manner similar to the irrigation probe discussed above. In other words, the distal end of the probe 30, carrying the distal extremity of the stent 20, is pushed from a punctum 2 to the nasal cavity 13. In this way, both the distal end and distal extremity traverse the lacrimal drainage system simultaneously.

Specifically, the distal end 72 of the combined structure is inserted horizontally through the punctum 2, canaliculus, and into the lacrimal sac 7. The structure is then oriented vertically and pushed down the nasolacrimal duct 8 into the nasal cavity 13 out the duct opening 9 into the nasal cavity until it hits the nasal floor 11 while the proximal end of the structure remains proximally external to the punctum. Further, this step of the procedure is accomplished by manipulation of the proximal portion of the structure outside the lacrimal drainage system.

The duct in the drawing is shown in an oversized state for clarity. Typically, the duct would closely conform to the combined stent/probe structure. In this example, the structure is inserted into the superior punctum and canaliculus, but would work similarly in the inferior punctum and canaliculus. Placement is accomplished with greater confidence having just completed the insertion of the irrigation probe during the passageway confirmation step.

Once the surgeon observes that the proximal end 23 of the stent 20 is in the punctum 2, with only the proximal flange 29 of the anchor structure remaining external to the punctum, he or she can be reasonably confident that the distal end 72 of the combined stent/probe structure has reached the nasal cavity 13.

At this point the surgeon has the option to pull slightly proximally on the probe while holding the anchor structure in place with a finger or other instrument in order to raise the distal end a distance 75 off the nasal floor 11 so that the nasal floor does not interfere with detachment of the stent from the probe 30. However, in most cases this step of raising the distal end is unnecessary.

Figure 9:
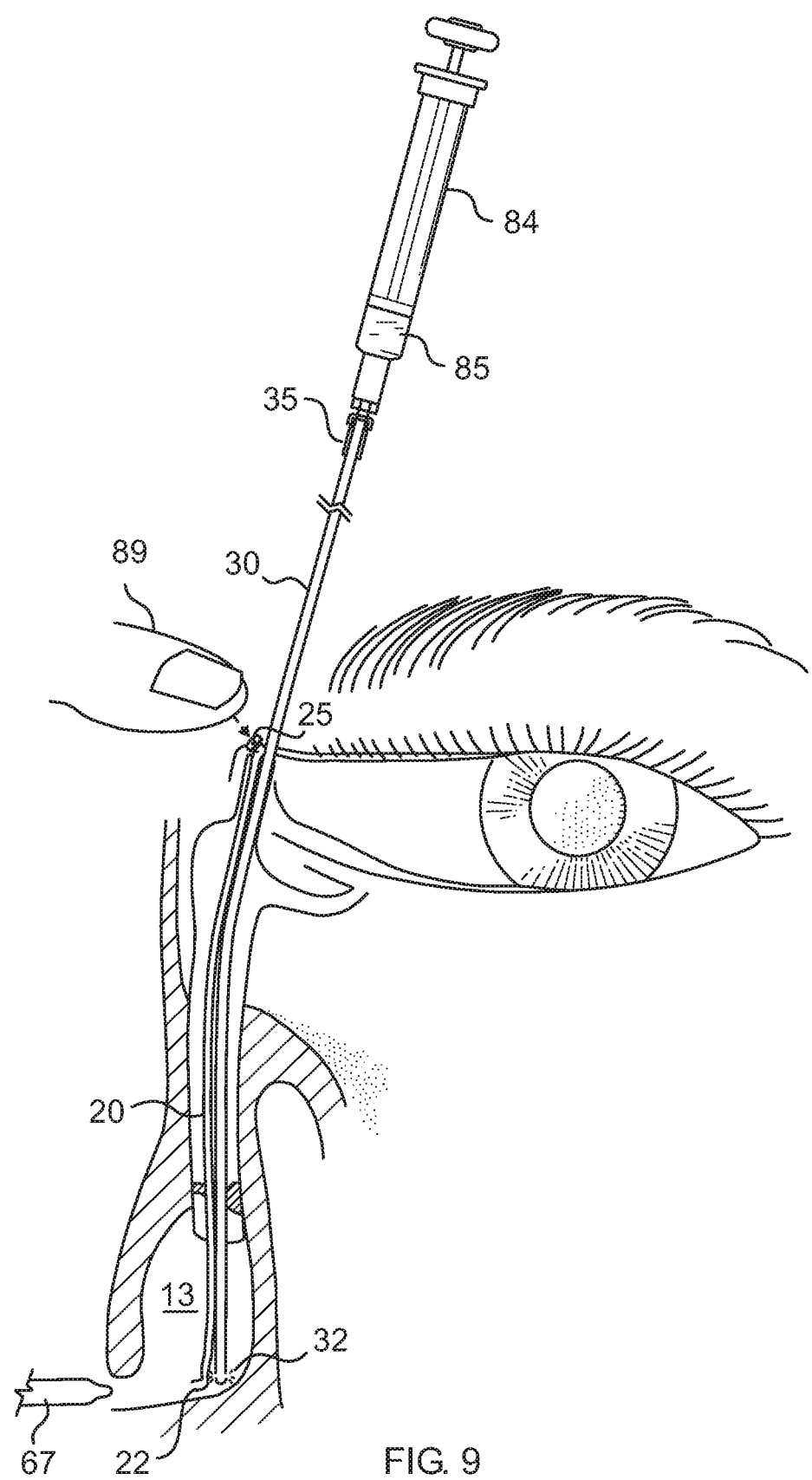
FIG. 9 illustrates disconnecting the distal end of the stent from the probe using the forced injection of fluid through the probe.

As shown in FIG. 9, the surgeon now connects a source of pressurized fluid to the probe 30. For example, a syringe 84 filled with fluorescein-stained fluid 85 is connected to the luer lock 35 at the proximal end of the probe. Pressurized fluid is injected through the internal channel of the probe. The fluid pressure builds until it overcomes the friction fit of the distal extremity 22 of the stent 20 thereby detaching it from the distal end 32 of the probe.

If a hollow dual open-ended tube is used for the stent 20, the surgeon can block the proximal aperture 25 of the stent using a finger 89 or other implement to prevent outflow of pressurized fluid during the detachment step. In many embodiments however, fluid will be prevented from flowing out the proximal end of the stent by built-in barriers in the lumen of the stent, or the stent not having a lumen extending its entire length.

Detachment of the distal extremity 22 of the stent 20 from the probe 30 can be confirmed by detecting an amount of injected fluid in the nose using a suction catheter 67. Further, in this way, the location of the distal end 32 of the probe and thus the now released distal extremity of the stent can be reconfirmed without visualization in the nasal cavity 13 and without contacting the distal end of the probe in the nasal cavity using another instrument.

Additional irrigation, suctioning, or delivery of medications can be performed through the probe after the stent has been disconnected.

Figure 10:
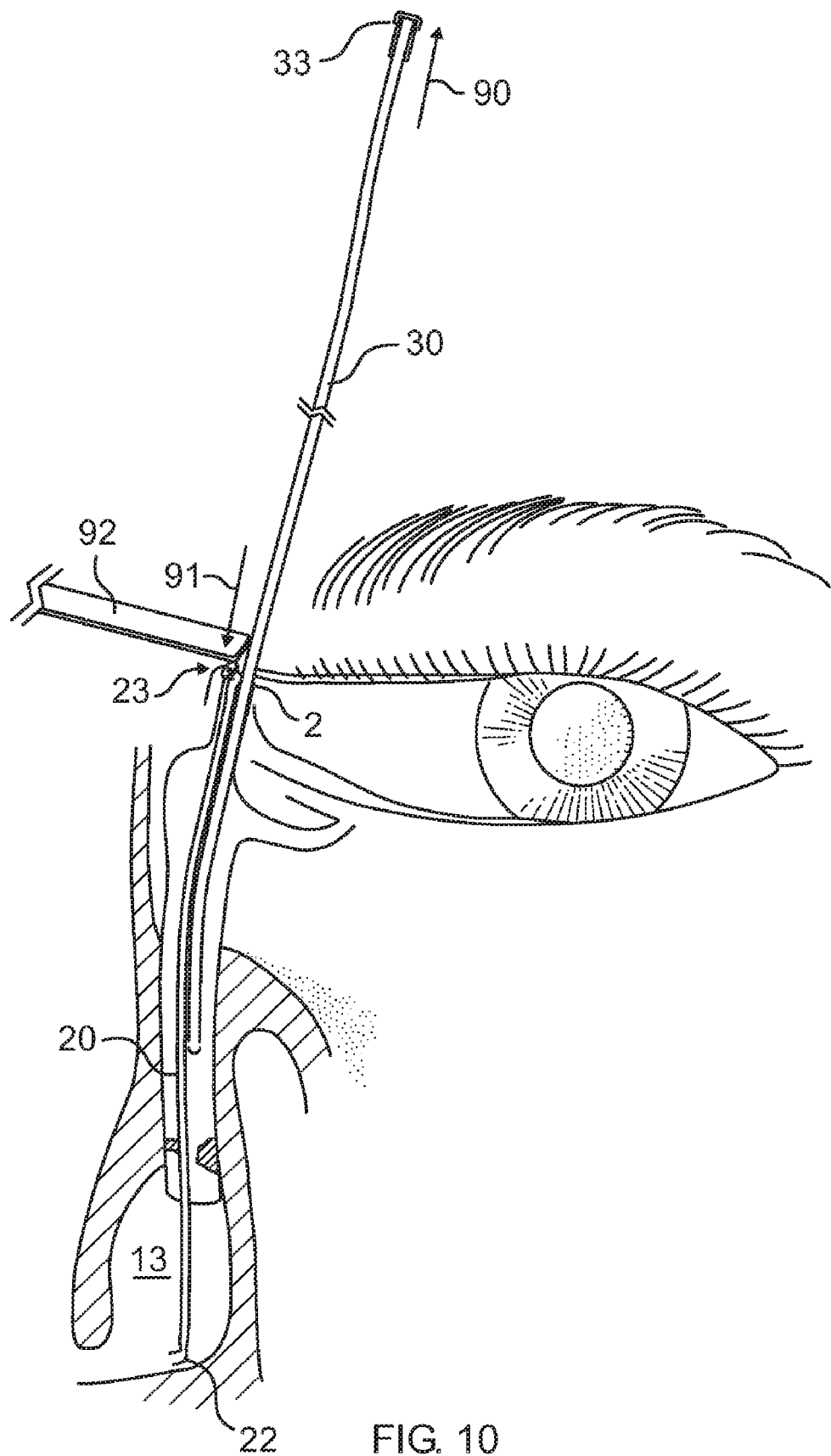
FIG. 10 illustrates withdrawing the probe while holding the stent in place.

FIG. 10 shows that the probe 30 is withdrawn while leaving the stent 20 in place. Specifically, the probe can be withdrawn out the punctum 2 by applying a withdrawing force 90 on the proximal end 33 of the probe while simultaneously applying a balancing, inserting force 91 on the proximal extremity 23 of the stent The surgeon can use a finger or other implement 92 to provide the balancing force. This causes the probe to move proximally with respect to the substantially stationary stent so that the stent remains in place with its distal end 22 in the nasal cavity 13.

While the probe is being withdrawn, further suction, irrigation, or delivery of medication can be provided to the various parts of the lacrimal drainage system that the tip of the probe passes on its way out.

It should be understood that the side-by-side configured combined stent and probe structure can be emplaced using a guide sleeve or other hollow tubular structure that has already been emplaced in the lacrimal drainage system.

After the probe is completely removed, the anchor structure should be in its proper position where the proximal flange rests against the outer rim of the punctum. However, if removal of the probe has slightly dislodged the anchor structure, the surgeon can push the anchor back into place. Alternately, where a separate punctal anchor structure apart from the stent is used, it can be inserted at this time.

Unlike prior devices and methods, placement of the stent can be accomplished in absence of visualization and in absence of retrieval of the distal extremity of the stent in the nose. Further, placement is accomplished in absence of any shortening of the distal end of the stent. In other words, the surgeon does not need to visualize or use any additional instruments in the nose, and does not need to cut the distal end to obtain the desired length.

It is important to note that the same, but shorter device can be used to stent one of the puncta, its canaliculus, the common canaliculus, lacrimal sac, and nasolacrimal duct depending on the intended post-operative length of the stent.

A further advantage of the instant device is that it can be reversibly emplaced in the lacrimal drainage system. In other words, the stent can be easily removed weeks or months later by grasping it with a forceps and pulling it out of the punctum during a typical office visit.

The combined stent/probe structure can also be used to emplace a stent during a dacryocystorhinostomy ("DCR"). In this case, the stent goes through one or both canaliculi and a prepared opening, directly into the nose. Stenting or intubation of the DCR passageway can be performed similarly to the previously described embodiments. Specifically, after a passageway is formed, the stent secured to the probe is pushed through the inferomedial wall of the lacrimal sac, lacrimal fossa, and lateral nasal wall into the nasal cavity. Emplacement is confirmed using the injection of a tracer fluid through the probe after the stent is disconnected, and further irrigation and/or suctioning may be conducted through the probe.

Referring now to FIGS. 11-12, there is shown an alternate embodiment of the side-by-side configured stent insertion structure 115 having a flexible stent 120 oriented in a side-by-side configuration to a hollow, semi-rigid lacrimal surgical probe 130. The distal extremity 122 of the stent is secured to the probe by being inserted through a small, undersized radial hole 138 formed through the probe sidewall near the probe's rounded distal end 132. It should be noted that the distal extremity of the stent does not need to be open as in the previously described embodiment. The resiliency of the stent material is relied upon to form a friction fit between the distal extremity of the stent and the distal end of the probe through the undersized hole.

In order to temporarily increase the flexural rigidity of the combined probe/stent structure 115 in this or other embodiments, a stiffening rod 140 having a rounded distal terminus 141 can be selected to coaxially engage the channel 134 of the probe 130. Therefore, the outside diameter of the rod is slightly smaller than the diameter of the probe channel. It should be noted that the rod can be pushed to the distal end of the probe, thereby contacting, and helping to hold in place, the distal extremity of the engaged stent 122 during insertion into the lacrimal drainage system. This can be useful when a stronger friction fit between the stent and probe is required or anticipated being needed.

Typically, the length of the rod is at least as long as the probe, and more preferably between about 0 and about 25 centimeters longer than the probe and can be made of stainless steel, Nitinol or other similar material known in the art. In most applications it is convenient to have the rod be about 10 centimeters longer than the probe. An optional manipulable flattened or otherwise enlarged section 142 at or near the proximal end of the rod, as can be found in many surgical probes, can be used to facilitate its handling. Use of the rod further allows for the use of a probe having a thinner wall, which can be less than 90%, often less than 75%, and sometimes even less than 50% of the thickness required when no rod is present. A thinner wall reduces material cost, and provides a less intrusive cross-section.

It should be understood that a stiffening rod can used in the embodiment of the probe of FIG. 4. However, care should be taken so that the distal terminus 141 of the rod does not penetrate so far as to dislodge the stent from the tip of the probe inadvertently. Such a rod can be used to purposefully dislodge the stent from the probe at the appropriate time. The rod can be marked on its outer surface to have an indicator showing where further penetration of the rod into the probe will cause the stent to dislodge. Optionally, the rod can be further adapted to have a removable barrier such as a clamp 144 which prevents insertion beyond a given distance until the barrier is removed.

The combined stent and probe structure 115 is inserted through the lacrimal drainage system in a manner similar to the previous exemplary embodiment.

As shown in FIG. 12, once the combined structure is emplaced, the surgeon first removes any rigidizing rod. Next, the surgeon disconnects the stent 120 from the probe 130 by inserting a stylet 150 through the channel 134 of the probe to cut away the distal portion 129 of the stent extending into the channel of the probe, thereby allowing the remaining stent to separate from the probe. Care should be taken to properly orient the stylet within the probe or otherwise shape its cutting tip 151 so that the stent is cut close to the hole.

As shown in FIG. 13, the combined stent/probe structure 152 can use a probe 153 having a rounded distal end 154 and an internal channel 155 which has a distal bend 156 in communication with a distal radial hole 157. In this way, pressurized fluid or a rod 158 can be used to dislodge a solid stent 159 having its distal extremity engaging the opening (as shown), or to dislodge a hollow tubular stent secured in the fashion of FIG. 3. If a rod is used, care should be taken to make the bend gradual enough to allow flexion of the rod.

As shown in FIG. 14, the probe 160 can be adapted to have an optional rounded collar 161 extending radially outwardly near the distal end 162 of the probe in order to provide a stronger friction fit between an over-the-probe-end stent. Those skilled in the art will recognize the optional use of other equivalent friction adjusting structures.

FIG. 15 shows an embodiment where the probe 165 has a rounded distal end 166 having an axial opening 167 of a smaller diameter the diameter of the internal channel 168. In this embodiment a rigidizing rod 169 can be used without fear of accidentally dislodging an over-the-probe-end stent by over insertion of the rod. The stent can be dislodged using a pressurized fluid.

Referring now to FIGS. 16A-16E, there are shown various alternate embodiments of the proximal extremity of the stent formed into a punctal anchor structure.

Figure 16A:
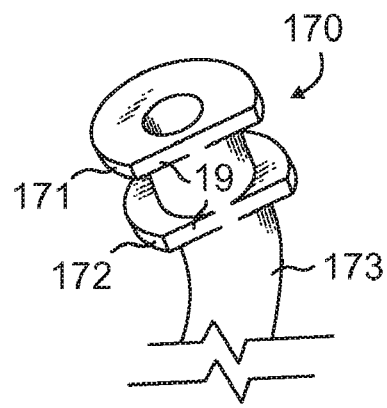
FIG. 16A-16E illustrates various integrated punctal anchor structures at the proximal extemity of the stent.

In FIG. 16A, the anchor structure 170 is characterized by a pair of spaced-apart, diametrically widened flanges 171,172. The proximal flange 171 is intended to rest against the outer rim of the punctum while the inner, distal flange 172 enlarges to rest against the internal interface between the canaliculus and the punctum. It should be noted that both flanges can be circular, elliptical or oval in shape. In the present embodiment the flanges are semi-circular having a flattened edge 19 which is substantially tangent to the substantially cylindrical outer surface of the body 173 of the stent. This allows for greater lateral movement of the anchor structure with respect to the probe during insertion of the combined stent/probe structure. In other words, the anchor can be said to have a radial disuniformity which allows it to more closely rest against a medial sidewall of said probe, thereby minimizing a lateral dimension of the combined probe/stent structure in its side-by-side configuration.

Figure 16B:
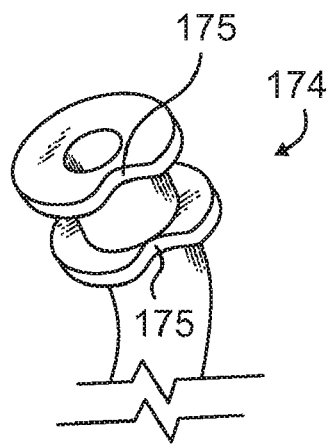

In FIG. 16B, the anchor structure 174 both flanges are shaped to include a substantially semicircular notch 175 for nesting against the outer cylindrical wall of the probe. The notches allow the stent to nest intimately with the cylindrical outer surface of the body of the probe in order to help minimize the diametric radial cross-sectional of the combined stent/probe structure especially when the anchor structure passes into the punctum along side the probe.

Figure 16C:
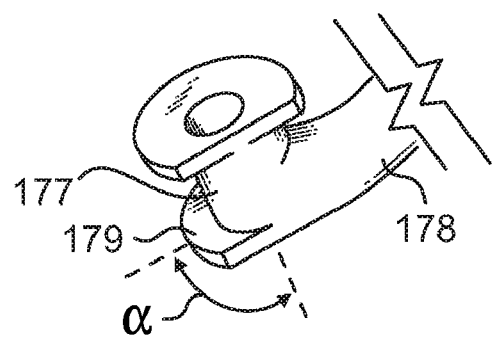

In FIG. 16C, the anchor stem 177 is oriented at an angle α to the body 178 of the stent of about 90 degrees. In this case the more distal flange 179 forms a protuberance as an extension of the stent body beyond the outer surface of the stem.

Figure 16D:
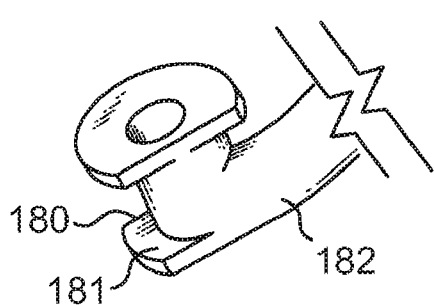

In FIG. 16D, the far edge 180 of the distal flange 181 is flattened as is the near edge to form a protuberance having width more closely matching the diameter of the stent body 182.

Figure 16E:
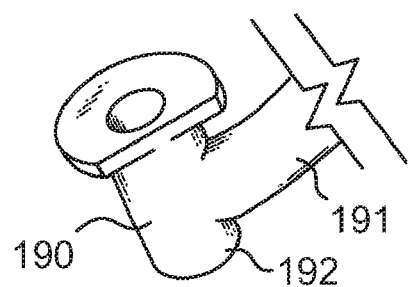

In FIG. 16E the anchor stem 190 is extended a distance beyond the transition to the orthogonally oriented stent body 191 to form a protuberance 192. At rest, the protuberance is sized and shaped to engage the anatomy of the canaliculus to keep the anchor from extruding.

While the preferred embodiment of the invention has been described, modifications can be made and other embodiments may be devised without departing from the spirit of the invention and the scope of the appended claims.

What is claimed is:

1. A method for placing a stent in a patient's nasolacrimal duct which comprises the steps of:
   selecting an elongated semirigid tubular probe and an elongated flexible stent;
     wherein said probe has a proximal end and a distal end;
     wherein said stent has a proximal extremity and a distal extremity;
     wherein said distal extremity is detachably secured to said distal end; and,
     wherein said probe and said stent are oriented in a side-by-side configuration;
   pushing said distal end and said distal extremity through a patient's punctum, canaliculus, lacrimal sac, nasolacrimal duct and into the nasal cavity;
   detaching said distal extremity from said distal end while said distal end is located in said cavity;
   proximally withdrawing said probe while leaving said distal extremity in said cavity; and,
   placing a punctal anchor associated with said proximal extremity within said patient's punctum.

2. The method of claim 1, wherein method further comprises:
   said probe having an internal channel, and a first opening to said channel near said proximal end; and a second opening to said channel near said distal end; and,
   wherein said stent occludes said second opening of said channel.

3. The method of claim 2, wherein said second opening comprises an axial hole extending through an endwall of said probe to said channel.

4. The method of claim 2, wherein said second opening comprises at least one radial hole extending through a sidewall of said probe to said channel.

5. The method of claim 2, wherein said detaching comprises:
   injecting a fluid into said channel at a pressure sufficient to overcome a force detachably securing said distal extremity to said distal end.

6. The method of claim 2, wherein said detaching comprises:
   inserting a rod into said channel and contacting said distal extremity at a pressure sufficient to overcome a force detachably securing said distal extremity to said distal end.

7. The method of claim 2, which further comprises:
   stiffening said probe prior to said pushing;
   wherein said stiffening comprises:
     engaging said channel with an oblong rod having a first flexural rigidity which is more rigid than a second flexural rigidity of said stent.

8. The method of claim 1, wherein said selecting an elongated flexible stent further comprises:
   choosing said stent to be tubular; and,
   wherein said distal extremity is open, and shaped and dimensioned to snugly fit over said distal end of said probe.

9. The method of claim 1, wherein said selecting comprises:
   determining a given length for said stent, wherein said determining comprises measuring a distance from said punctum to said nasal cavity;
   wherein said measuring comprises:
     inserting a graduated probe through said punctum to said nasal cavity;
     confirming a distal end of said graduated probe is located in said nasal cavity, and,
     identifying a graduation mark on said graduated probe closest to the punctal opening.

10. The method of claim 1, wherein said selecting of said probe comprises:
    choosing said probe to have at least one radial hole near said distal end of said probe and wherein said distal extremity engages said hole.

11. The method of claim 10, wherein said detaching comprises pushing a stylet into said channel to cut said stent.

12. The method of claim 1, wherein said method is practiced in absence of retrieving a portion of said stent out the naris.

13. The method of claim 1, wherein said method is practiced in absence of visualizing said stent within said nasal cavity.

14. The method of claim 1, wherein said method is practiced in absence of shortening said stent in vivo.

15. The method of claim 1, wherein said placing a punctal anchor occurs during said pushing step.

16. The method of claim 1, wherein said method further comprises:
    confirming that the distal end is located in said nasal cavity;
    wherein said confirming comprises:
      injecting a tracing fluid through the probe; and
      recovering traces of said fluid in said nasal cavity.

17. The method of claim 1, which further comprises injecting medication into said system through said probe.

18. A method for stenting a passageway formed by dacryocystorhinostomy ("DCR") which comprises the steps of:
    selecting an elongated tubular probe and an elongated flexible stent;
      wherein said probe has an open proximal end and an open distal end, and defines an internal channel; and,
      wherein said stent has a proximal extremity and a distal extremity; and,
      wherein said distal extremity is detachably secured to said distal end;
    pushing said probe carrying said stent through said passageway and into the nasal cavity;
    confirming that the distal end of said probe is located in said nasal cavity;
    detaching said distal extemity from said distal end;
    proximally withdrawing said probe while leaving said stent in place; and,
    placing a punctal anchor associated with a proximal extremity of said stent within said patient's punctum.

* * * * *